United States Patent
Mihara et al.

(10) Patent No.: US 6,807,248 B2
(45) Date of Patent: Oct. 19, 2004

(54) MULTISOURCE TYPE X-RAY CT APPARATUS

(75) Inventors: Kazumasa Mihara, Hiroshima-ken (JP); Susumu Urano, Hiroshima-ken (JP); Keiichi Hori, Hyogo-ken (JP); Shin Ogura, Tokyo (JP)

(73) Assignee: Mitsubishi Heavy Industries, Ltd., Tokyo (JP)

( * ) Notice: Subject to any disclaimer, the term of this patent is extended or adjusted under 35 U.S.C. 154(b) by 0 days.

(21) Appl. No.: 10/302,835

(22) Filed: Nov. 25, 2002

(65) Prior Publication Data

US 2003/0072407 A1 Apr. 17, 2003

Related U.S. Application Data

(63) Continuation of application No. PCT/JP02/01837, filed on Feb. 28, 2002.

(30) Foreign Application Priority Data

Feb. 28, 2001 (JP) ......................................... 2001-055312

(51) Int. Cl.[7] ................................................. H05G 1/60
(52) U.S. Cl. ............................ 378/10; 378/9; 378/134; 378/136; 378/138
(58) Field of Search .......................... 378/10, 122, 124, 378/134, 136, 137, 138, 143, 146

(56) References Cited

U.S. PATENT DOCUMENTS

| | | | | |
|---|---|---|---|---|
| 4,239,972 A | * | 12/1980 | Wagner ........................... | 378/9 |
| 4,274,005 A | * | 6/1981 | Yamamura et al. ............. | 378/9 |
| 4,866,745 A | * | 9/1989 | Akai ............................. | 378/9 |
| 5,125,012 A | * | 6/1992 | Schittenhelm ................. | 378/10 |
| 5,142,652 A | * | 8/1992 | Reichenberger et al. ..... | 378/136 |
| 5,218,624 A | * | 6/1993 | LeMay ........................ | 378/10 |
| 5,259,014 A | * | 11/1993 | Brettschneider ............ | 378/138 |
| 5,446,799 A | * | 8/1995 | Tuy ............................ | 382/132 |
| 5,475,729 A | * | 12/1995 | Mattson et al. ............. | 378/135 |
| 5,481,585 A | * | 1/1996 | Kimura et al. ............. | 378/134 |
| 5,633,906 A | * | 5/1997 | Hell et al. .................. | 378/10 |
| 6,181,765 B1 | * | 1/2001 | Sribar et al. ................ | 378/10 |
| 6,333,968 B1 | * | 12/2001 | Whitlock et al. ........... | 378/136 |
| 6,385,292 B1 | * | 5/2002 | Dunham et al. ............ | 378/122 |
| 6,731,716 B2 | * | 5/2004 | Mihara et al. ............... | 378/9 |

FOREIGN PATENT DOCUMENTS

| | | |
|---|---|---|
| JP | 53-103392 | 9/1978 |
| JP | 54-38787 | 3/1979 |
| JP | 55-46408 | 4/1980 |
| JP | 10-75944 | 3/1998 |
| JP | 10-295682 | 11/1998 |

* cited by examiner

*Primary Examiner*—Edward J. Glick
*Assistant Examiner*—Allen C. Ho
(74) *Attorney, Agent, or Firm*—Armstrong, Kratz, Quintos, Hanson & Brooks, LLP

(57) ABSTRACT

A multisource type X-ray CT apparatus including a fixed sensor array, a fixed vacuum chamber, and an X-ray generation unit. The X-ray generation unit includes a cathode and an anode which are fixed in the vacuum chamber so as to surround the sensor array, a gate array including a plurality of grid electrodes which are densely fixed between the cathode and anode and which include holes for passing the electron beams, a power source which applies a bias voltage to the grid electrodes of the gate array, and a controller which controls the power supply operation from the power source so as to select the grid electrode suitable for image pickup from the gate array in accordance with an image pickup portion of the subject and to release the bias voltage applied to the selected grid electrode.

7 Claims, 12 Drawing Sheets

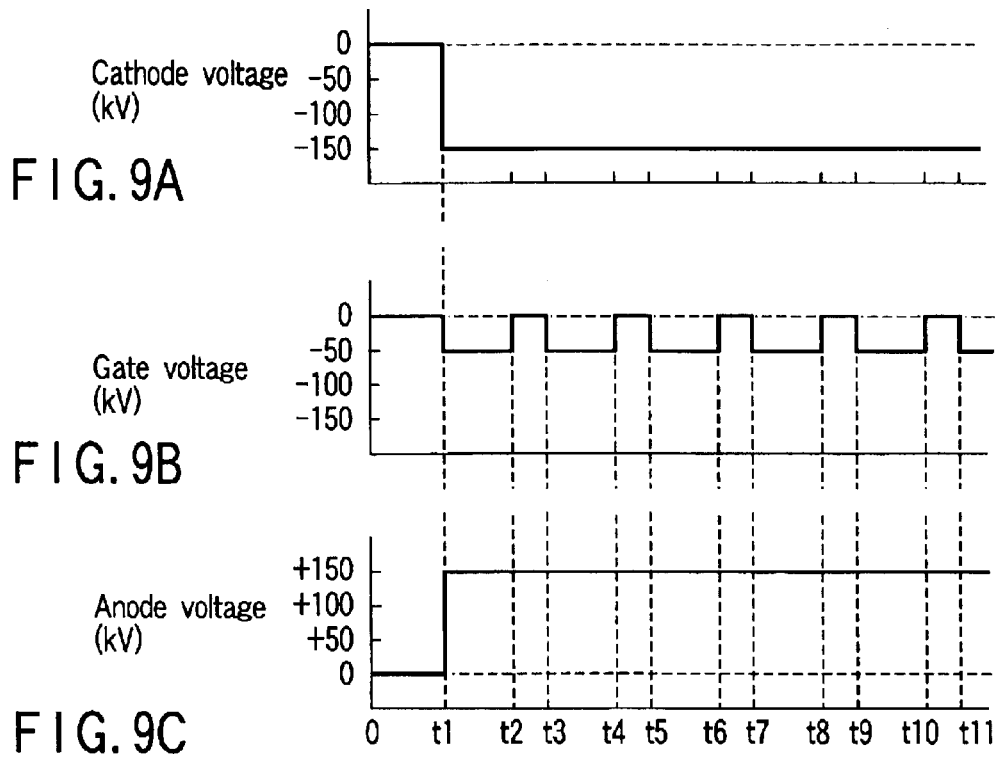
FIG. 9A
FIG. 9B
FIG. 9C
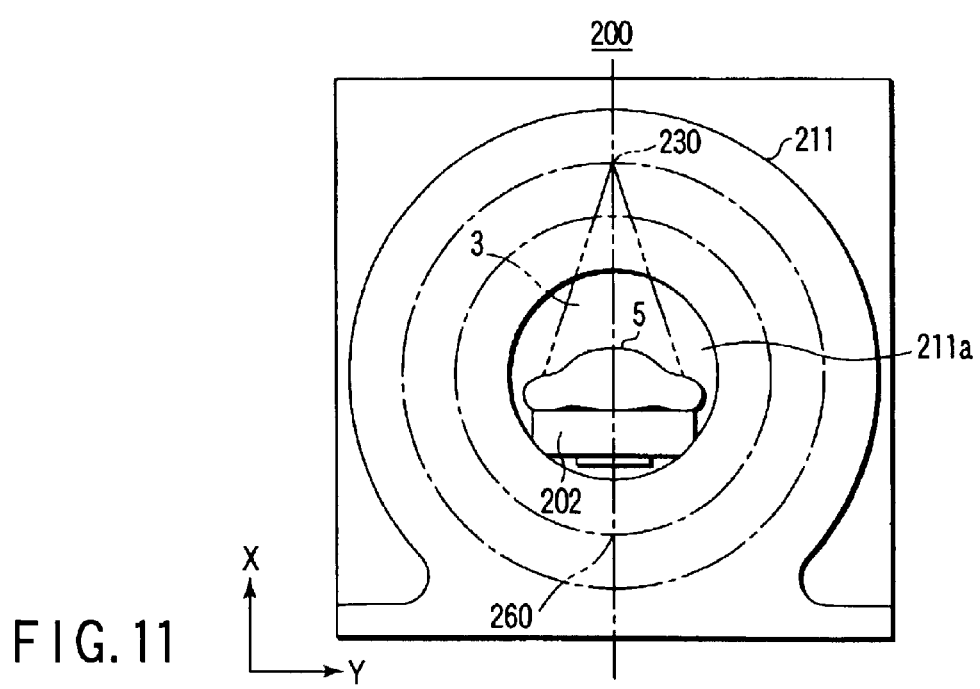
FIG. 11

MULTISOURCE TYPE X-RAY CT APPARATUS

CROSS-REFERENCE TO RELATED APPLICATIONS

This is a Continuation Application of PCT Application No. PCT/JP02/01837, filed Feb. 28, 2002, which was not published under PCT Article 21(2) in English.

This application is based upon and claims the benefit of priority from the prior Japanese Patent Application No. 2001-055312, filed Feb. 28, 2001, the entire contents of which are incorporated herein by reference.

BACKGROUND OF THE INVENTION

1. Field of the Invention

The present invention relates to a multisource type X-ray CT apparatus for use in three-dimensional image diagnosis.

2. Description of the Related Art

For a high-speed X-ray CT scanner, by using an electron beam control system for electrically turning X-ray generation on and off, the scan time of a certain X-ray CT scanner has heretofore been remarkably accelerated ($1/60$ to $1/2000$ second), and tomography of a measurement object has been performed. This high-speed X-ray CT scanner is proposed as an image diagnosis apparatus (multisource type X-ray CT apparatus) including a large number of X-ray sources, for example, in Jpn. Pat. Appln. KOKAI Publication Nos. 10-295682 and 10-075944.

As shown in FIG. 1, a conventional multisource type X-ray CT apparatus includes: a plurality of detectors 102 arranged and fixed at equal pitch intervals in a concentric circle which surrounds an image pickup area 104; a vacuum chamber 105 which is disposed further outside so as to surround a group of detectors 102 and which has a double tube structure; a plurality of X-ray generation units 101 to 132 contained in the vacuum chamber 105; and an X-ray generation control apparatus (not shown). The X-ray generation units 101 to 132 include 32 3-pole vacuum tubes densely arranged in the concentric circle, and each unit irradiates a subject (not shown) disposed in the image pickup area 104 with fan-beam X-rays (fan beams) 3.

The X-ray generation control apparatus includes 32 pulse generation control ports which have a one-to-one correspondence with pulse generators disposed for the respective X-ray generation units 101 to 132, selects the X-ray generation unit optimum for image pickup based on predetermined input data, and controls the on/off switching of a power supply circuit at a high speed so that the fan-beam X-rays 3 (spread angle $2\alpha$) are emitted only from the selected X-ray generation unit.

The fan-beam X-rays 3 emitted from the X-ray generation unit are passed through the subject (not shown) of the image pickup area 104 and one incident upon the detectors 102 on a back side. Thereby a transmitted X-ray amount is detected. Detection signals are sent to a data storage apparatus from the detectors 102, stored in the data storage apparatus, and processed by a data processing apparatus. Data obtained by processing the signals is reproduced as an X-ray tomography image on a display.

However, in the conventional apparatus, installation space is restricted by spatial arrangement in relation to the subject, sizes of the vacuum chamber, X-ray generation unit, and detector are limited, and therefore the number of X-ray generation units which can be arranged is limited. Therefore, a large number of X-ray generation units cannot densely be arranged, space resolution of the apparatus cannot be enhanced, and therefore the image reproduced from the transmitted X-ray data is blurred.

Moreover, in each X-ray generation unit of the conventional apparatus, the cathode, anode, and gate (grid electrode) require power supply circuits, and the power source capacity becomes enormous. Particularly when the space resolution is enhanced, the total number of power supply circuits is vast. This causes the problem that not only the manufacturing cost but also the running cost of the power supply circuit increase.

BRIEF SUMMARY OF THE INVENTION

The present invention has been developed to solve the above-described problem, and an object thereof is to provide a multisource type X-ray CT apparatus in which a high space resolution is fulfilled in a limited installation space, a clear image can be obtained, and manufacturing and running costs can be reduced.

According to the present invention, there is provided a multisource type X-ray CT apparatus comprising: a sensor array including a plurality of detection devices densely fixed on a circumference which surrounds a subject in order to detect X-rays transmitted through the subject; a vacuum chamber fixed so as to surround the sensor array coaxially with arrangement of the sensor array; and an X-ray generation unit which is disposed in the vacuum chamber and which emits X-rays toward the subject surrounded by the sensor array.

The X-ray generation unit includes: a circular-arc or linear cathode which is fixed/disposed in the vacuum chamber so as to surround the sensor array coaxially with the arrangement of the sensor array and which emits electron beams by power supply; a circular-arc or linear anode disposed in a position upon which the electron beams emitted from the cathode are incident, and fixed/disposed in the vacuum chamber so as to surround the sensor array coaxially with the arrangement of the sensor array, so that the electron beams are received and the X-rays are emitted; a gate array including a plurality of grid electrodes which are densely fixed between the cathode and anode and which include holes for sucking and passing the electron beams emitted from the cathode; a power source which applies a bias voltage to the grid electrodes of the gate array; and control means for controlling a power supply operation from the power source so as to select the grid electrode suitable for image pickup from the gate array in accordance with an image pickup portion of the subject and to release the bias voltage applied to the selected grid electrode.

In this case, the gate array may include 60 to 240 grid electrodes, further include 150 to 300 grid electrodes, and further include 240 to 500 grid electrodes. With an increase of the number of grid electrodes, resolution of the image pickup portion is enhanced and the image becomes clear. For example, it is possible to obtain an X-ray CT section image of blood vessels such as an artery. On the other hand, when the number of grid electrodes is increased in the gate array, the width per grid electrode is excessively narrowed, and this makes it difficult to form the electron beam passing holes. Moreover, the X-ray generation unit is limited by the ceiling height of the room where the unit is installed. Since the diameter of the unit cannot needlessly be enlarged, the increase of the number of grid electrodes is limited to some degree. Therefore, an upper limit of the number of grid electrodes in the gate array is set to 500.

A method of forming the gate array comprises: laminating a layer of a high-melting metal or alloy on a ceramic ring substrate using a physical or chemical vapor deposition method; and subsequently using a wet or dry etching method to partially remove the layer of the high-melting metal or alloy and form the grid electrodes whose adjacent portions are insulated from one another.

It is preferable to use materials having high pressure resistance and insulating properties, such as silicon nitride ($Si_3N_4$), silicon oxide ($SiO_2$), silicon carbide (SiC), alumina ($Al_2O_3$), and sialon (SiAlON) in the ceramic ring substrate. Especially, high-purity alumina is suitable as the insulating material having high pressure resistance for the ceramic ring substrate.

A single metal such as tungsten, molybdenum, and tantalum is preferably used in the high-melting metal, and an alloy containing one or two or more of tungsten, molybdenum, and tantalum as a main component is preferably used in the high-melting alloy.

It is preferable to use various CVD methods, an ion plating method, and a sputtering method in the physical or chemical vapor deposition method. Additionally, it is especially preferable to use a plasma CVD method among various CVD methods. Because a metal or alloy layer formed by the plasma CVD method is suitable to remove by the dry etching in which photolithography is used.

Furthermore, the electron beam passing holes are preferably made in the grid electrodes by machining. It is preferable to appropriately select the diameter of each electron beam passing hole in a range of 1 to 5 mm in accordance with the size of the grid electrode.

The cathode may be a combination of a plurality of circular-arc or linear segment electrodes arranged on the same circumference, or may be a single annular electrode. When the cathode includes a plurality of circular-arc or linear segment electrodes, the grid electrodes of the gate array are divided into groups including the same number of electrodes. A control circuit is preferably constituted in which the grid electrodes of each group are allocated to the corresponding segment electrodes. Additionally, metal materials such as W, BaW, NiCr alloy, NiCrCo alloy, and NiCrFe alloy, or nonmetal materials such as $LaB_6$ may be used in a cathode material.

Moreover, similarly as the cathode, the anode may also be a combination of a plurality of circular-arc or linear segment electrodes arranged on the same circumference. The corresponding anode is divided into several segment blocks similarly as the cathode and the operation of each block can be controlled. Additionally, it is general to use tungsten or a tungsten alloy in the anode material.

According to the present invention, there is provided a multisource type X-ray CT apparatus comprising:

a donut-shaped gantry to define a space for diagnosis in which a subject is inserted along an axial center;

an annular vacuum tube disposed along a circumference of a concentric circle centering on the axial center in the gantry;

a cathode array including a plurality of discharge electrodes which are disposed in the vacuum tube and densely fixed over at least a half circumference having a center angle of 180° along the circumference of the concentric circle centering on the axial center;

an anode array including a plurality of target electrodes which are disposed opposite to the discharge electrodes in the vacuum tube so as to have one-to-one correspondence with the discharge electrodes and densely fixed over at least the half circumference having the center angle of 180° along the circumference of the concentric circle centering on the axial center and which generate X-rays by incident electron beams emitted from the discharge electrodes;

a gate array including a plurality of grid electrodes which are disposed between the cathode array and anode array and which tolerate or limit passage of the electron beams toward the target electrodes from the discharge electrodes by control of an applied voltage;

a first insulating member which insulates the discharge electrodes of the cathode array from the vacuum tube;

a second insulating member which insulates the target electrodes of the anode array from the vacuum tube;

a third insulating member which insulates the grid electrodes of the gate array from the vacuum tube; and a plurality of X-ray detection portions densely fixed/arranged over at least the half circumference having the center angle of 180° along the circumference centering on the axial center so as to have one-to-one correspondence with the target electrodes of the anode array via the subject.

Additionally, the center angle of the arrangement of the X-ray detection portions is set to be larger than the center angle of the arrangement of the anode array or cathode array by an X-ray spread angle $2\alpha$. All that X-rays the pass through the subject are detected by the X-ray detection portions, so that much information is obtained.

The above-described first, second, and third insulating members are formed of continuous annular or circular-arc ceramic, and materials such as silicon nitride ($Si_3N_4$), silicon oxide ($SiO_2$), silicon carbide (SiC), alumina ($Al_2O_3$), and sialon (SiAlON) are preferably used. Particularly, it is preferable to use ceramic materials having high pressure resistance and insulating property, such as high-purity alumina.

BRIEF DESCRIPTION OF THE SEVERAL VIEWS OF THE DRAWING

FIGS. 9A to 9C are timing charts of an X-ray irradiation operation.

FIG. 11 is a schematic constitution diagram of the multisource type X-ray CT apparatus viewed from an X-axis direction.

DETAILED DESCRIPTION OF THE INVENTION

Preferred embodiments of the present invention will be described hereinafter with reference to the accompanying drawings.

First Embodiment

Figure 1:
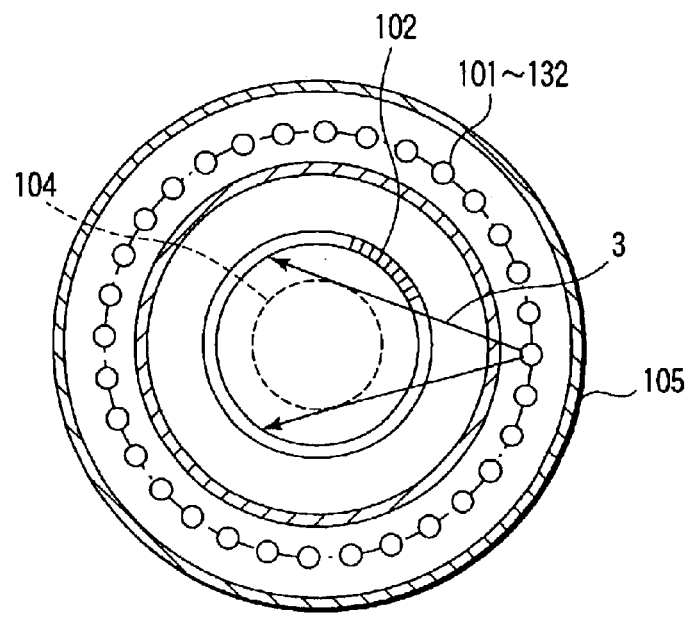
FIG. 1 is an inner perspective sectional view showing an outline of a conventional apparatus.
Figure 2:
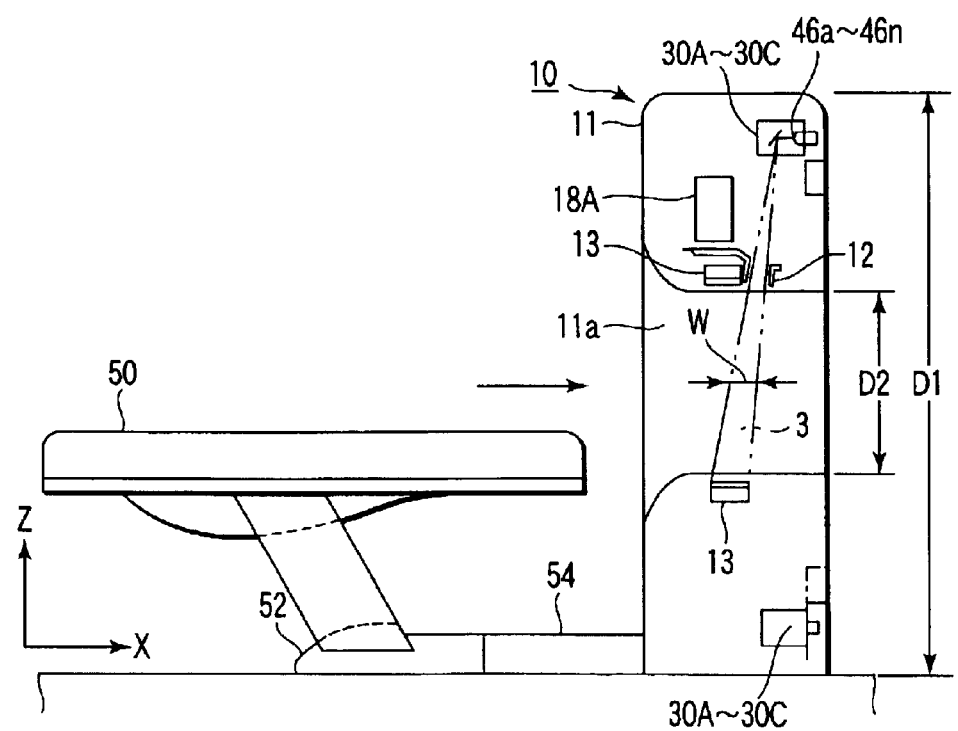
FIG. 2 is a constitution block diagram schematically showing an X-ray image diagnosis apparatus including a multisource type X-ray CT apparatus according to an embodiment of the present invention.
Figure 3:
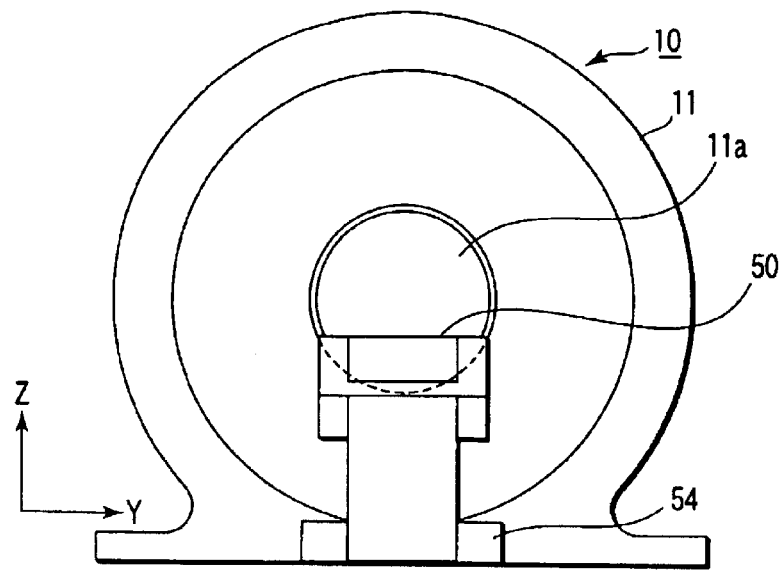
FIG. 3 is an outline view showing the apparatus of FIG. 2 viewed from an axial direction.

As shown in FIGS. 2 and 3, an X-ray image diagnosis apparatus for medical purposes 10 includes a cylindrical vacuum chamber 11 including X-ray generation units 30a, 30b, 30c, and is disposed in such a manner that a subject (patient) (not shown) is moved into or out of a space for diagnosis 11a in a vacuum chamber middle together with a movable bed 50. That is, the movable bed 50 is supported such that the bed can move along a guide rail 54 in an X-axis direction by a slider mechanism 52.

The inside of the vacuum chamber 11 is evacuated by a vacuum pump (not shown) via an exhaust port (not shown). Inside the vacuum chamber 11, the X-ray generation units 30a, 30b, 30c, a beam limiter 12, a sensor array (detector) 13, an image signal digitizer 18A, an electron gun driving circuit 42, and the like are disposed. Fan-shaped X-rays 3 emitted from the X-ray generation units 30a, 30b, 30c are narrowed by a collimator (not shown), further defined in a width W in an irradiation position by the beam limiter 12, passed through the subject disposed in the space for diagnosis 11a, and thereafter detected by the sensor array 13.

The sensor array 13 includes (2048×200) extra high sensitivity CdTe sensors densely fixed and arranged on a circumference surrounding the space for diagnosis 11a where the subject is disposed, and has a resolution of 0.5 mm. Additionally, an image pickup width W of one shot is about 80 mm. Moreover, the vacuum chamber 11 has an outer diameter D1 of 1900 to 2100 mm, and an inner diameter D2 of 550 to 750 mm.

The vacuum chamber 11 is fixed/disposed coaxially with the sensor array 13 and on an outer peripheral side of the sensor array 13. The inside of the vacuum chamber 11 is a vacuum, and three X-ray generation units 30A to 30C are densely arranged on the circumference inside the vacuum chamber 11. These X-ray generation units 30A to 30C and sensor array 13 are shifted in the X-axis direction and arranged, so that a radius (Z-axis) of the vacuum chamber 11 is irradiated with the X-rays 3 in a forward tilting direction in a fan shape. Therefore, the fan-shaped X-rays 3 are passed through the subject disposed in the space for diagnosis 11a and detected by the sensor array 13 on an opposite side (below) without being interrupted by the sensor array 13 on an X-ray irradiation side (above).

Figure 4:
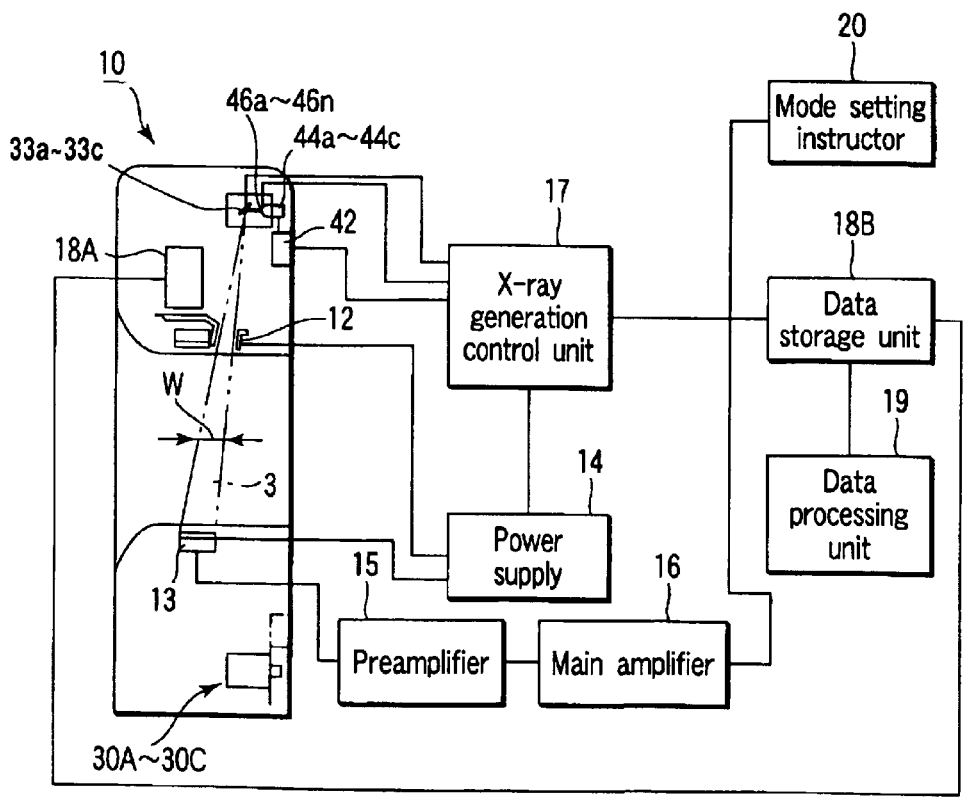
FIG. 4 is a block circuit diagram of the multisource type X-ray CT apparatus according to the embodiment of the present invention.

As shown in FIG. 4, an input side of an X-ray generation control apparatus 17 is connected to a data storage apparatus 18B and mode setting instructor 20. X-ray transmission information detected by the sensor arrays 13 is converted to a current signal proportional to a transmitted X-ray amount, and sent to and stored in the image signal digitizer 18A and data storage apparatus 18B via a preamplifier 15 and main amplifier 16. The stored data is output to a data processing apparatus 19 from the data storage apparatus 18B, and processed by the data processing apparatus 19. The processed data is reproduced/displayed as X-ray CT image information of the subject on a display (not shown).

On the other hand, an output side of the X-ray generation control apparatus 17 is connected to a power source 14 and anodes 33a to 33c, cathodes 44a to 44c, and grid electrodes 46a to 46n of the gate array in the X-ray generation units 30A to 30C. When at least one of the mode setting instructor 20 and data storage apparatus 18B outputs an X-ray generation command signal toward the X-ray generation control apparatus 17, the X-ray generation control apparatus 17 controls a power supply operation to the electron gun driving circuit 42 from the power source 14 based on the command, and selects the grid electrode suitable for the image pickup portion from a gate array 46. In response to this, any cathode of the X-ray generation units 30A, 30B, 30C emits an electron beam, the negative bias voltage applied to the selected grid electrode is canceled to obtain a zero potential, and the electron beams are passed through the holes in the grid electrode and incident upon the anode. When the electron beams are incident upon the anode, the anode generates a secondary X-ray, and the fan-shaped X-rays are emitted toward the subject via the collimator attached to a window.

The X-ray generation units will next be described with reference to FIGS. 5 to 7.

Figure 5:
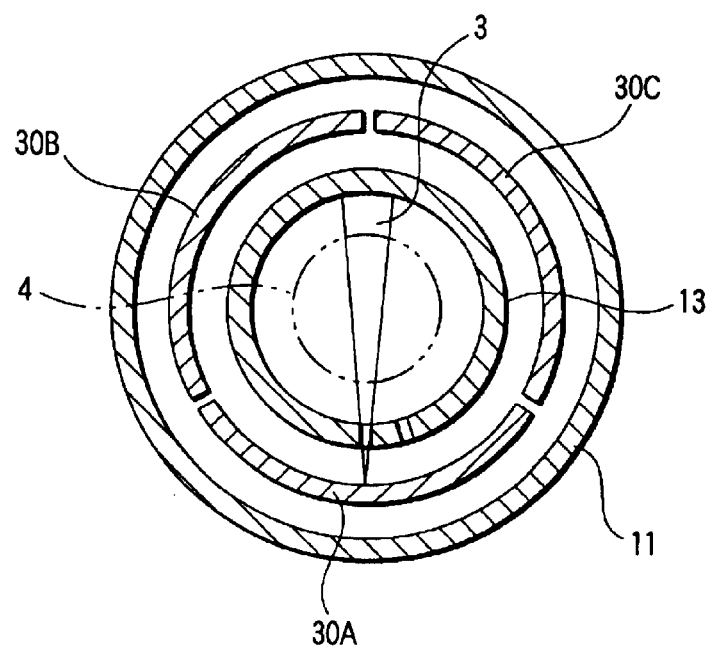
FIG. 5 is an inner perspective sectional view showing the outline of the multisource type X-ray CT apparatus according to the embodiment of the present invention.

As shown in FIG. 5, three X-ray generation units 30A, 30B, 30C having circular arc shapes are arranged on the circumference coaxial with the sensor array 13. The respective X-ray generation units 30A, 30B, 30C are connected to the electron gun driving circuit 42. Since three X-ray generation units 30A, 30B, 30C substantially have the same constitution, only the first X-ray generation unit 30A will be described as a representative with reference to FIGS. 5 and 6, and the description of the other units 30B, 30C is omitted.

Figure 6:
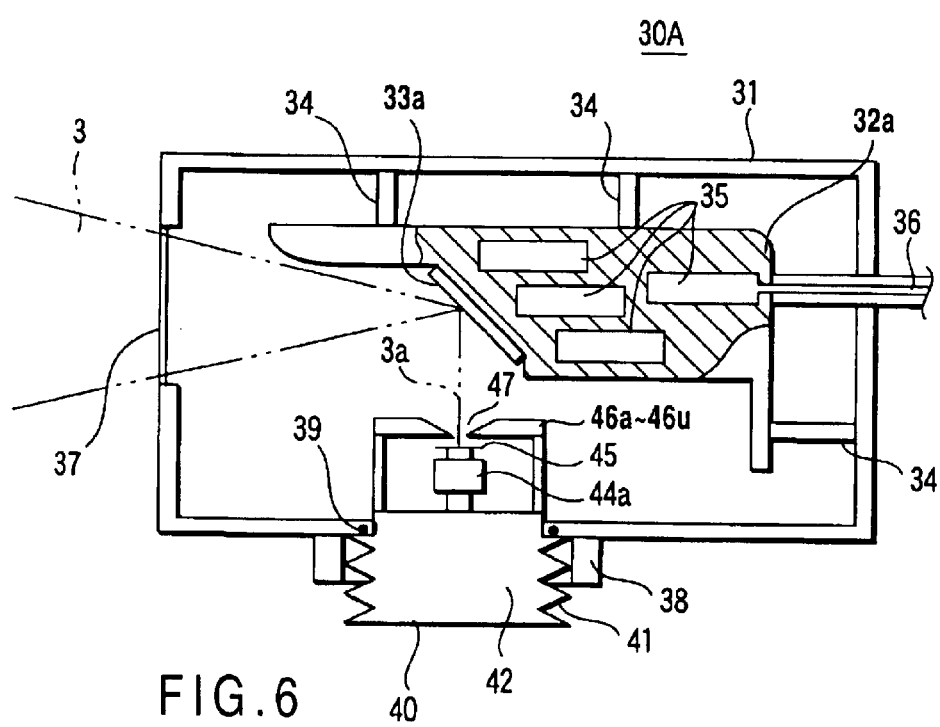
FIG. 6 is a major part perspective sectional view of the multisource type X-ray CT apparatus according to the embodiment of the present invention.

As shown in FIG. 6, the X-ray generation unit 30A essentially has a structure similar to that of a 3-pole X-ray tube, and includes the anode 33a, cathode 44a and a plurality of grid electrodes 46a to 46u as major elements in a vacuum container 31. The apparatus of the present invention is characterized in that each X-ray generation unit includes a plurality of grid electrodes 46a to 46u having controllable potentials. A first group of grid electrodes 46a to 46u are densely arranged on the same circumference together with second and third groups of grid electrodes 46v to 46w, 46m to 46n of the X-ray generation units 30B, 30C, and constitute the gate array 46. The gate array 46 of the present embodiment includes 240 (80 electrodes×3) grid electrodes 46a to 46n.

An opening is formed in one side surface of the annular or circular-arc vacuum container 31, and a hold portion 38 including a female thread groove is attached to the periphery of the opening. A gate/cathode unit 40 including an engagement portion 41 of a male thread groove is inserted in the opening, and the male thread groove of the engagement portion 41 meshes with the female thread groove of the hold portion 38, so that the gate/cathode unit 40 is attached to the vacuum container 31. Additionally, an O ring 39 is inserted between the gate/cathode unit 40 and the side wall of the vacuum container 31, and air tightness is maintained inside the container. Moreover, the hold portion 38 and engagement portion 41 preferably have a screw-in structure of a bayonet system, but attachment/detachment mechanisms of other structures such as a usual screw-in structure, flange joint structure, and ball joint structure may also be used.

The electron gun driving circuit 42, the cathode 44a, and the first group of grid electrodes 46a to 46u as a part of the gate array are attached to the gate/cathode unit 40. A linearly extended filament 45 is used in the cathode 44a. This filament 45 is connected to the electron gun driving circuit 42. Upon receiving the power supply from the power source 14 controlled by the X-ray generation control apparatus 17, the filament 45 emits an electron beam 3a.

Figure 7:
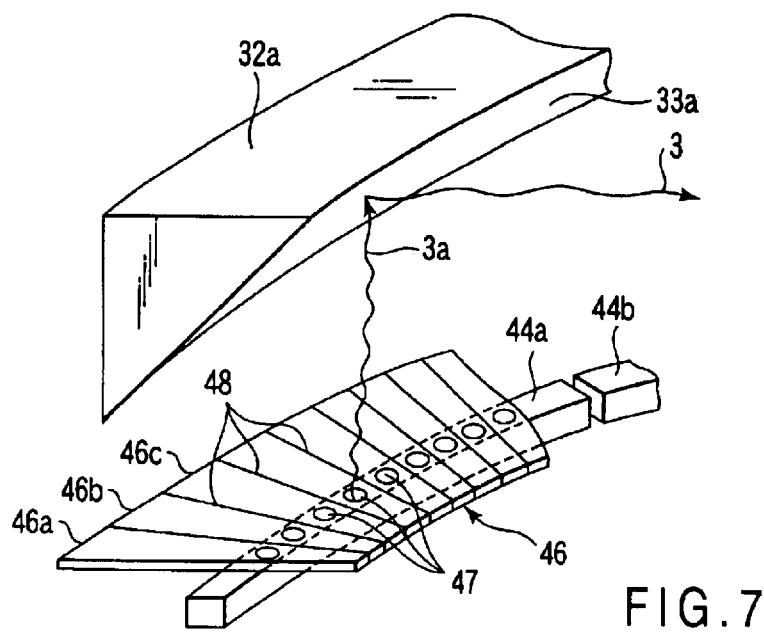
FIG. 7 is an exploded perspective view schematically showing a major part of the multisource type X-ray CT apparatus according to the embodiment of the present invention.

As shown in FIG. 7, electron beam passing holes 47 are formed in the respective grid electrodes 46a to 46n of the gate array. The strip-shaped grid electrodes 46a, 46b, . . . 46n disposed adjacent to each other are insulated from each other via insulating portions 48. A manufacturing method of the gate array 46 comprises: laminating a high-melting metal or alloy such as tungsten, molybdenum, and tantalum on a ceramic ring substrate such as silicon nitride ($Si_3N_4$), silicon oxide ($SiO_2$), silicon carbide (SiC), alumina ($Al_2O_3$), and sialon (SiAlON) using a physical or chemical vapor deposition method such as a plasma CVD method; and subsequently using a wet or dry etching method to partially remove an electrical conducting layer of the high-melting metal or alloy and form the insulating portions 48. Additionally, it is preferable to drill the electron beam passing holes 47 by the mechanical processing after forming and partially etching the electrical conducting layer, but the holes may be drilled/made beforehand before the film formation or partial etching. In this case, the diameter of each electron beam passing hole 47 is limited by the width dimension of the grid electrode, but is preferably about 1 to 5 mm from a viewpoint of a perforation processing operation property, and is more preferably about 2 to 4 mm in order to pass a sufficient amount of electron beams 3a. In the present embodiment, the diameter of the electron beam passing hole 47 is set to 3±0.5 mm.

A control circuit of the gate array will next be described with reference to FIG. 8.

The anodes 33a to 33c, cathodes 44a to 44c, and grid electrodes 46a to 46n of the gate array in the X-ray generation units 30A to 30C are n pulse generation control ports 26a to 26n via n pulse generators 25a to 25n disposed in the X-ray generation control apparatus 17. A CPU (not shown) for sending signals to the pulse generation control ports 26a to 26n and performing a control is connected to the mode setting instructor 20. When the mode setting instructor 20 inputs a setting mode signal into the CPU of the X-ray generation control apparatus 17, the CPU sends X-ray generation command signals to the pulse generation control ports 26a to 26n in accordance with a set mode, and the signal is transmitted to the pulse generator corresponding to the pulse generation control port having received the command signal. The negative bias voltage applied to the corresponding grid electrode is canceled to obtain the zero potential. Thereby, the electron beam 3a is passed only through the hole 47 of the corresponding grid electrode and incident upon the anode 33a, and the X-ray is emitted.

Additionally, two pulse generators disposed opposite to each other via the subject on the circumference are connected to one pulse generation control port. When one pulse generation control port is connected to two pulse generators corresponding to two X-ray generation units disposed opposite to each other, two grid electrodes can synchronously be controlled to be ON/OFF, and two shots of images can be picked up at the same time. When the signals are sent to these pulse generation control ports 26a to 26n, it is possible to transmit the signals to the pulse generators 25a to 25n. Moreover, one pulse generation control port is connected to two pulse generators. Therefore, when one signal is given to the pulse generation control port, the signal can simultaneously be transmitted to two pulse generators, and two X-ray generation units disposed opposite to each other can simultaneously emit the X-rays. Additionally, three or more grid electrodes may simultaneously be subjected to the ON/OFF control as long as areas upon which the X-rays are simultaneously incident do not overlap each other.

As shown in FIG. 6, the anode 33a is attached to the inclined surface of a cooling block 32a, cooled, and prevented from being damaged by heat received from the electron beam 3a. That is, coolant channels 35 are formed inside the cooling block 32a, and a cooling oil is supplied to the coolant channels 35 from a supply source (not shown) via a supply path 36. Additionally, the cooling block 32a is formed of a conductor excellent in thermal conductivity, such as copper and aluminum, and is therefore supported by a plurality of insulating support members 34 so as to be insulated from the vacuum container 31.

The anode 33a is formed of a tungsten electrode plate as an electron beam target, and positioned in such a manner that a surface against which an electron convergent onto the target collides forms a focal point. The high-speed electron rushes into the target atom and is stopped from moving, and a part of energy of movement is discharged as an X-ray. That is, during the X-ray generation, when the electron beam 3a is incident upon the anode 33a from the cathode 44a, the fan-shaped X-ray 3 is emitted in a direction of reflection from the anode 33a in accordance with the surface angle. Additionally, a beryllium window 37 is attached to an inner peripheral surface of the annular or circular-arc vacuum container 31, and the fan-shaped X-ray 3 is emitted toward the subject via the window 37. Moreover, a collimator (not shown) is attached to the periphery of the window 37, and the fan-shaped X-ray 3 is narrowed in a desired irradiation range.

An operation of the apparatus will next be described with reference to timing charts of FIGS. 9A to 9C.

When the main switch of the apparatus 10 is turned ON at time t1, as shown in FIG. 9A, a bias voltage of minus 150 kV (this can also be −20 V) is applied as a voltage sufficient for heating the cathode at a temperature sufficient for discharging a significant electron amount to the cathodes 44a to 44c. As shown in FIG. 9B, the bias voltage, for example, of minus 50 kV (this can also be −1 kV) is applied to the gate array 46. As shown in FIG. 9C, the bias voltage of plus 150 kV is applied to the anodes 33a to 33c. At time t2, the mode setting instructor 20 or data storage apparatus 18B shown in FIG. 4 outputs a command signal indicating first X-ray generation to the X-ray generation control apparatus 17.

Figure 8:
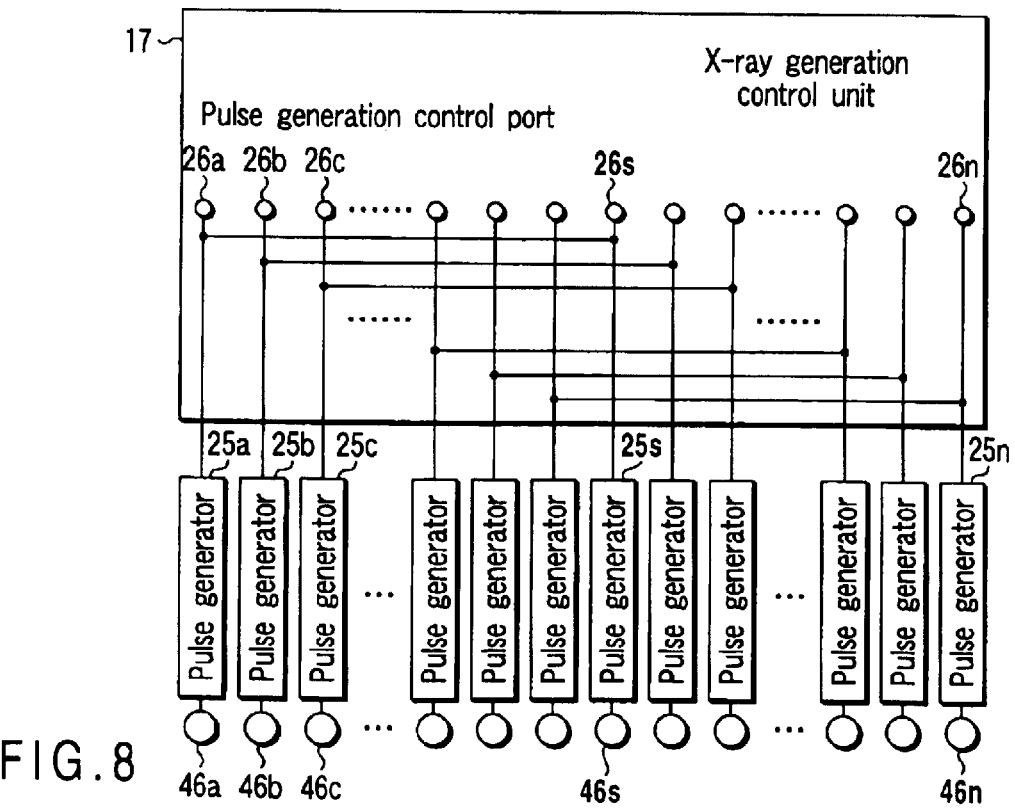
FIG. 8 is a block circuit diagram for controlling an operation of a gate array including a large number of grid electrodes.

Based on this first command, the command of the first X-ray generation is inputted into the pulse generation control port 26a in the X-ray generation control apparatus 17 shown in FIG. 8. Upon receiving the input signal, two pulse generators 25a, 25s simultaneously generate pulse waves, and supply these pulse signals to the grid electrodes 46a, 46s corresponding to the pulse generators 25a, 25s. When the pulse generation signal is received, the negative bias voltages of the grid electrodes 46a, 46s are canceled to obtain the zero potential, and the electron beam 3a is passed through the holes 47 and incident upon the anodes 33a, 33s. At time t3, the command of the first X-ray generation ends, the negative bias voltages of the grid electrodes 46a, 46s are restored, and the electron beam 3a is again shut off by the gate array 46. For a time t2 to t3, the anodes 33a, 33s emit the fan-shaped X-rays 3. In this manner, an operation of successively changing the emission place of the X-ray is repeated.

Times t3 to t4, t5 to t6, t7 to t8, t9 to t10 are gate change times, and each time is controlled in a range of 2.1 to 20.8 microseconds (1/480,000 to 1/48,000 second).

Moreover, times t2 to t3, t4 to t5, t6 to t7, t8 to t9, t10 to t11 are X-ray generation times (image pickup times), and the X-ray generation time is controlled in a range of 1.4 to 13.9 microseconds (1/720,000 to 1/72,000) which corresponds to 2/3 of the gate change time t3 to t4, t5 to t6, t7 to t8, t9 to t10.

The generated fan-shaped X-ray 3 is emitted toward a subject 5 in the space for diagnosis 11a. The emitted fan-shaped X-ray 3 is absorbed in accordance with the transmittance of the subject, and detected by the sensor arrays 13 disposed opposite to each other on the circumference.

The X-ray transmission information detected by the sensor arrays 13 is converted to a current signal proportional to the transmitted X-ray amount, thereafter amplified by the preamplifier 15 and main amplifier 16, and sent as a voltage signal to the data storage apparatus 18B.

When the detection operation by the sensor arrays 13 ends, next a command for second X-ray generation is input into the pulse generation control port in the X-ray generation control apparatus 17, and the detection operation is performed similarly as described above. Moreover, when the X-ray transmission information obtained from all successively performed detection operations is detected by the sensor arrays 13, the information is converted to the current signal in proportion to the transmitted X-ray amount, and processed in the data processing apparatus 19 via the preamplifier 15, main amplifier 16, and data storage apparatus 18B. X-ray CT image information of the subject 5 is obtained from the data subjected to the signal processing.

When the gate array 46 including a large number of grid electrodes 46a to 46n are disposed inside the vacuum chamber 11 in this manner, the X-ray can be generated in a desired irradiation direction in the vacuum chamber 11. Therefore, X-ray generation points can be arranged more densely, and adjacent image pickup intervals can be set finely. Therefore, with the increase of a scan speed, an image quality can be enhanced by improving a space resolution, and it is possible to recognize details of the inner structure of the measurement object.

Additionally, the use of three X-ray generation units has been described in the present embodiment, but the number is not limited, and one, two or four units may be used.

As described above, according to the present invention, a high space resolution can be fulfilled in a limited installation space, and manufacturing and running costs can be reduced. Moreover, with the increase of the scan speed, the image quality can be enhanced by the space resolution improvement, and it is possible to diagnose the details of the inner structure of the subject.

Second Embodiment

A second embodiment of the present invention will be described hereinafter with reference to FIGS. 10 to 20.

Figure 10:
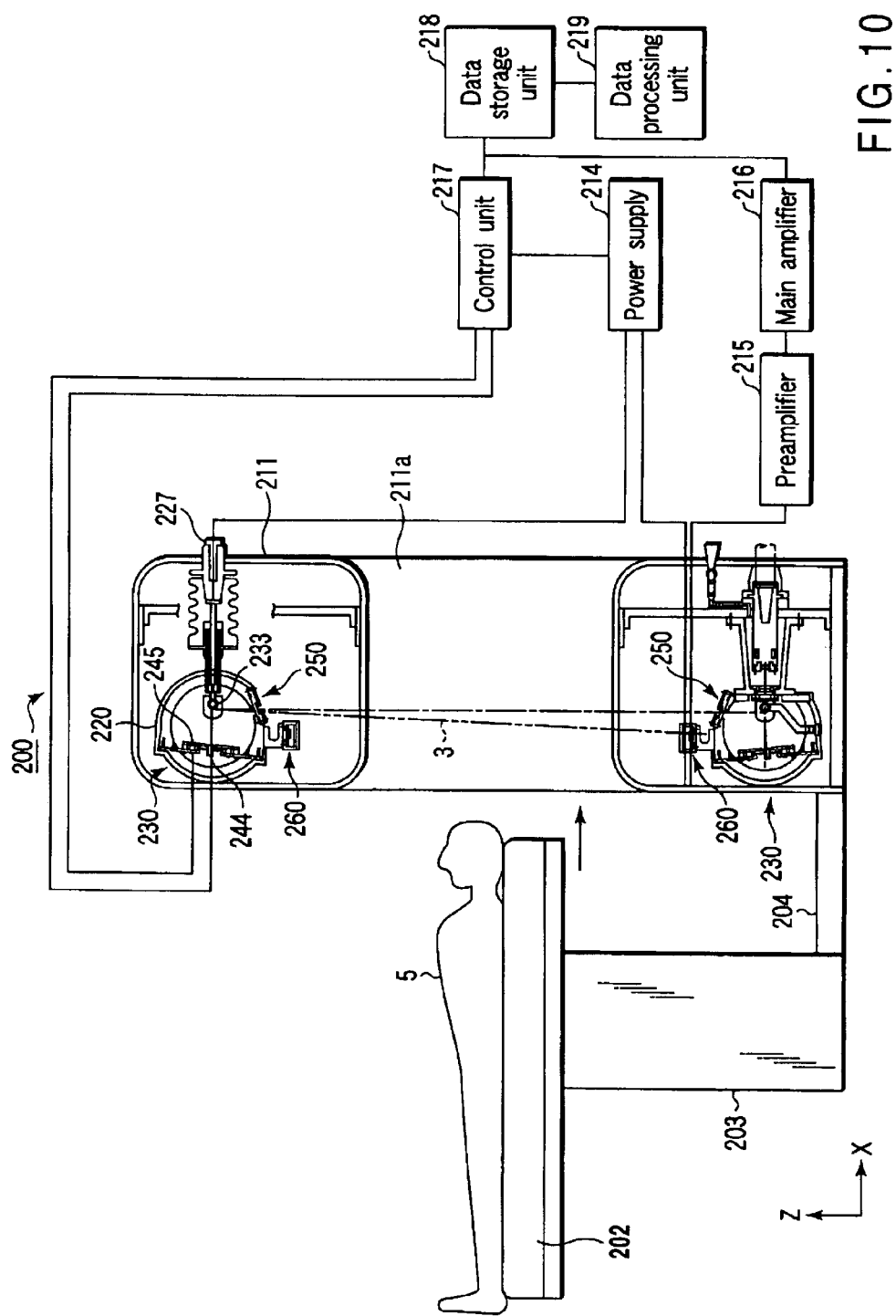
FIG. 10 is a constitution block diagram schematically showing the X-ray image diagnosis apparatus including the multisource type X-ray CT apparatus according to the embodiment of the present invention.

As shown in FIGS. 10 and 11, a multisource type X-ray CT apparatus 200 includes a donut-shaped gantry 211 including an X-ray generator 230 and radiation detector 260, and is disposed in such a manner that the patient 5 as the subject is inserted into or out of a space for diagnosis 211a in a gantry middle together with a movable bed 202. That is, the movable bed 202 is supported so as to be movable along a guide rail 204 in the X-axis direction by a slider mechanism 203.

In the gantry 211, the X-ray generator 230 having an output of 150 kV, beam limiter (not shown), detector 260, image signal digitizer (not shown), electron gun driving circuit (not shown), and the like are disposed. The X-ray generator 230 is contained in a vacuum tube 220. The vacuum tube 220 includes a continuous annular hollow portion over a whole circumference of 360°. The vacuum tube 220 is formed of nonmagnetic stainless steel having a thickness of 5 mm.

Figure 13:
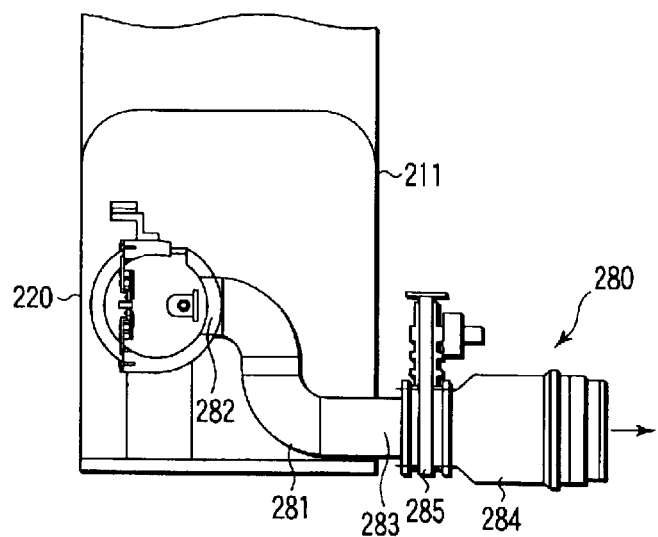
FIG. 13 is an inner perspective sectional view showing an exhaust channel of a vacuum container.

As shown in FIG. 13, a tube 281 of an exhaust mechanism 280 is introduced into the gantry 211 via a gantry side opening 283, and connected to an exhaust port 282 of the vacuum tube 220. The tube 281 is connected to a large-diameter tube 284 via a valve 285, and the large-diameter tube 284 is further connected to a suck-in port of a vacuum pump (not shown). This pump (not shown) has a capability of evacuating the inside of the tube 220 until an inner pressure of the vacuum tube 220 reaches $1 \times 10^{-7}$ to $1 \times 10^{-9}$ Torr.

A terminal 227 is introduced into the gantry 211 through the side wall of the gantry, and is connected to the electron gun driving circuit, gate array (grid) driving circuit, and anode (target) driving circuit of the X-ray generator 230. The terminal 227 is connected to an external power source 214 whose operation is controlled by a control apparatus 217.

Figure 15:
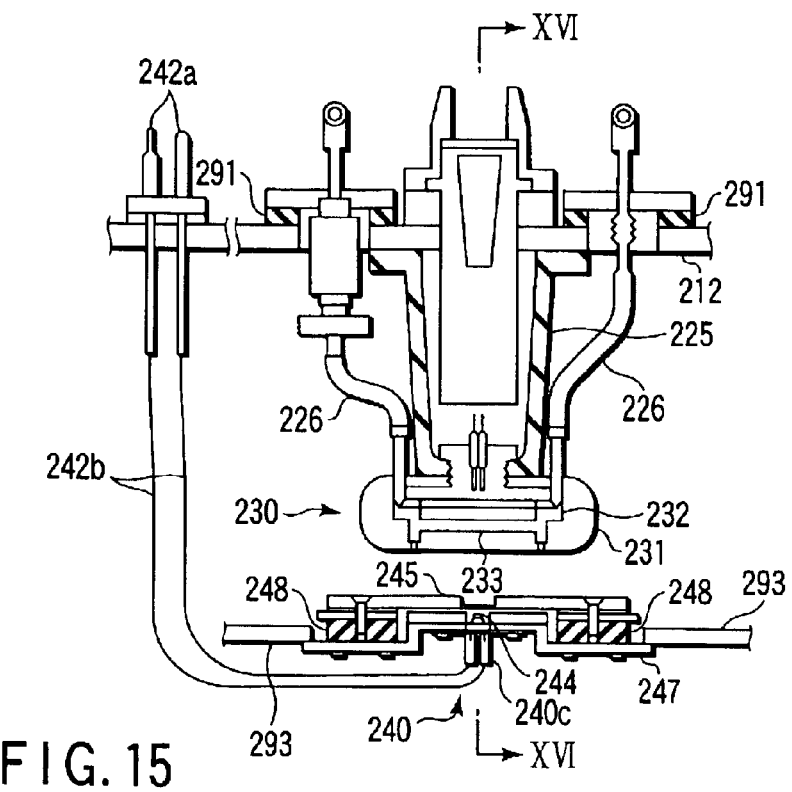
FIG. 15 is a major part sectional view of the multisource type X-ray CT apparatus according to the embodiment of the present invention.
Figure 16:
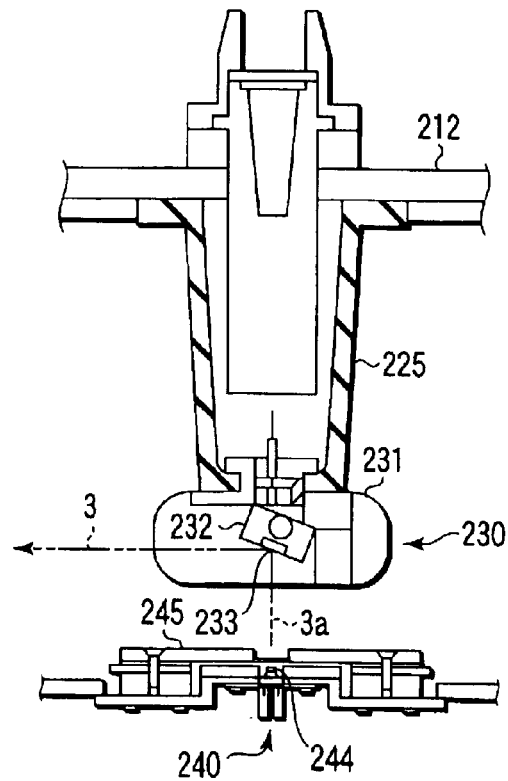
FIG. 16 is a major part sectional view showing the multisource type X-ray CT apparatus viewed along arrows XVI—XVI in FIG. 15.
Figure 17:
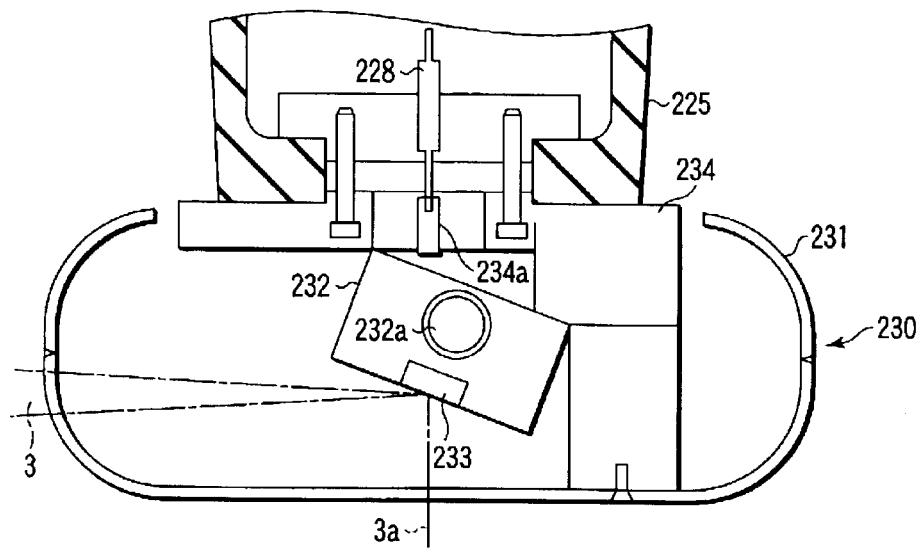
FIG. 17 is an enlarged sectional view showing an X-ray generation portion.

As shown in FIGS. 15 to 17, the terminal 227 is connected to a plurality of Cu electrode rods 228, and the tip end of each Cu electrode rod 228 is pressed onto a power supply point 234a of an anode block 234.

The terminal 227 and Cu electrode rods 228 are insulated from peripheral members by an insulator 225. The insulator 225 is formed of high-purity alumina ($Al_2O_3$) having a high pressure resistance property, and has a pressure resistance capability of 150 to 200 kV.

Figure 12:
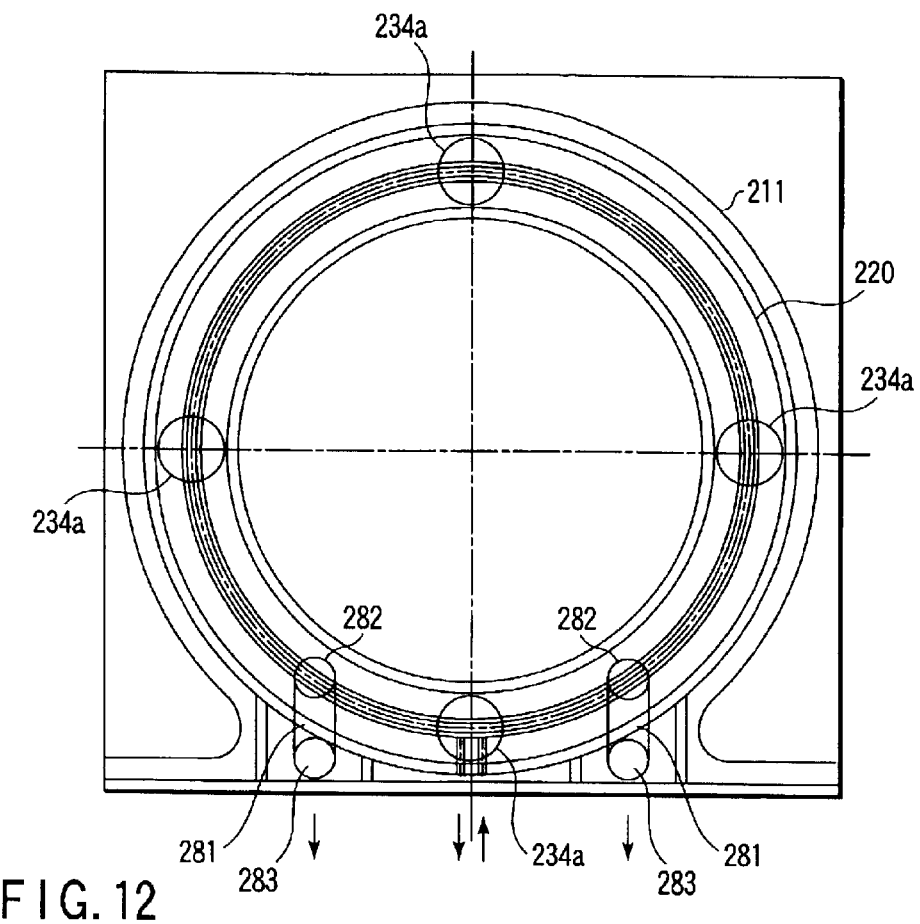
FIG. 12 is an inner perspective sectional view schematically showing the multisource type X-ray CT apparatus viewed from the X-axis direction.

As shown in FIG. 12, the power supply points 234a are distributed/arranged in four positions of 0°, 90°, 180°, 270° of the anode block 234. A high pressure direct current of 150 kV is supplied between anode (target) 233 and cathode 244 from the power source 214 via these four power supply points 234a. This multipoint power supply system is used, and any X-ray generator 230 emits the X-ray 3 having substantially the same operation at substantially the same timing.

The X-ray 3 emitted from the X-ray generator 230 is narrowed by the collimator (not shown), defined in a predetermined diameter by the beam limiter (not shown), emitted toward the subject 5 disposed in the space for diagnosis 11a, passed through the subject 5, and subsequently detected by the detector 260.

The detector 260 includes 2048 to 4078 extra high sensitivity CdTe monocrystal photoelectric conversion devices 272 densely fixed and arranged on the concentric circle which surrounds the space for diagnosis 211a, and has a resolution of 0.3 mm. Additionally, an image pickup width of one shot is about 500 mm. Moreover, the gantry 211 has an outer diameter of about 2000 mm, and inner diameter of 800 to 1000 mm.

As shown in FIG. 11, the X-ray generators 230 are arranged on the concentric circle outside the circumference on which a plurality of detectors 260 are arranged.

Figure 14:
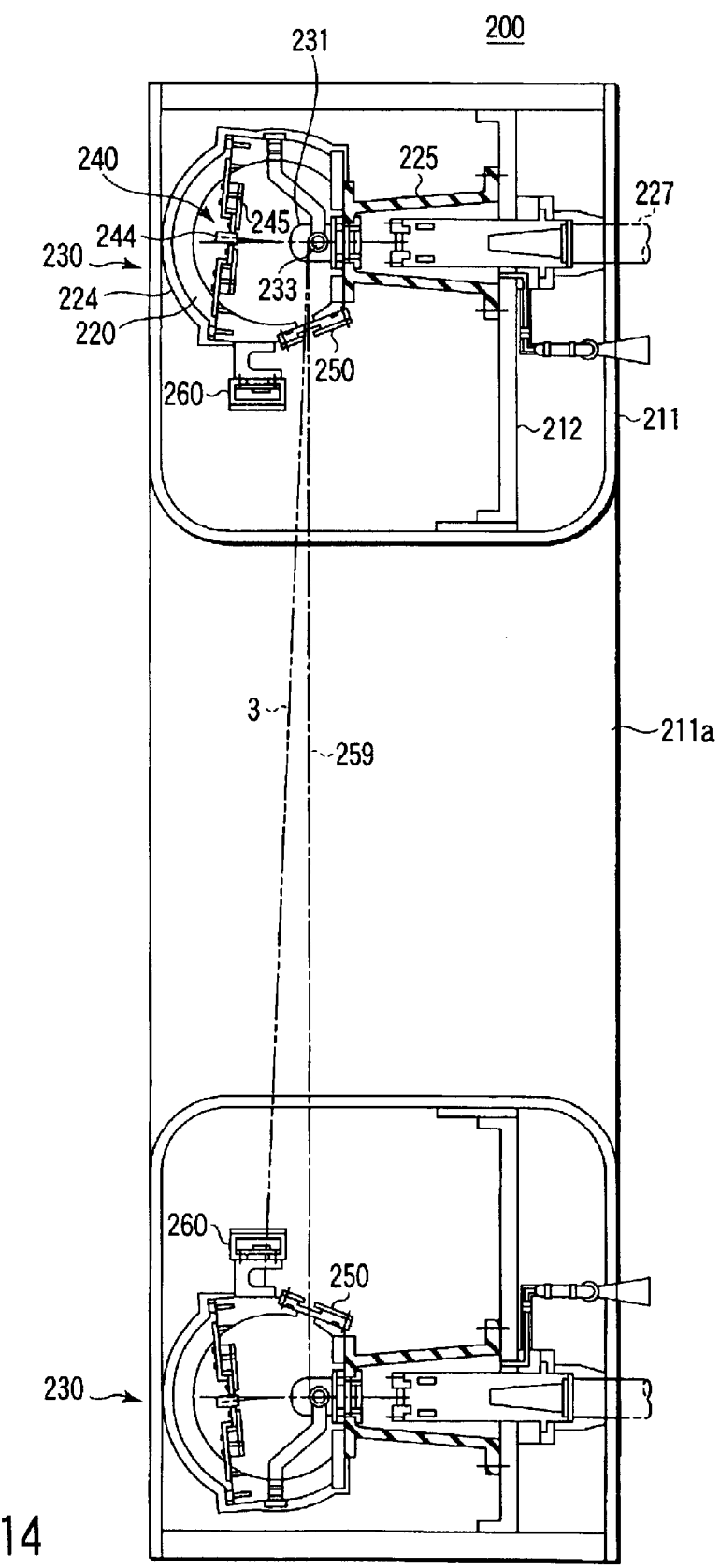
FIG. 14 is an inner perspective sectional view showing the multisource type X-ray CT apparatus (150 kV) according to the embodiment of the present invention.

These X-ray generator 230 and detector 260 are slightly shifted in the X-axis direction, and as shown in FIGS. 10 and 14, the X-ray 3 is emitted in a slightly forward tilting direction with respect to the radius (Z-axis) of the gantry 211. Therefore, the X-ray 3 is passed through the subject 5 disposed in the space for diagnosis 211a and detected by the radiation detector 260 on the opposite side (below) without being interrupted by the radiation detector 260 on the X-ray emission side (above).

As shown in FIG. 10, the input side of the control apparatus 217 including a digital calculation circuit is connected to a data storage apparatus 218. The X-ray transmission information detected by the radiation detectors 260 is photoelectrically converted to a current or voltage signal proportional to the transmitted X-ray amount, and sent to and stored in the data storage apparatus 218 and image signal digitizer (not shown) via a preamplifier 215 and main amplifier 216.

The stored data is output to a data processing apparatus 219 from the data storage apparatus 218, and processed in the data processing apparatus 219. The processed data is reproduced/displayed as the X-ray CT image information of the subject 5 on the display (not shown).

The output side of the control apparatus 217 is connected to the power source 214, and the anode (target) 233, cathode 244, and grid electrodes 245 as the gate array in the X-ray generator 230. When the data storage apparatus 218 outputs the X-ray generation command signal to the control apparatus 217, the control apparatus 217 controls the power supply operation to the electron gun driving circuit from the power source 214 based on the command, and selects the grid electrode disposed in a position suitable for the image pickup portion from a plurality of grid electrodes 245. Accordingly, any cathode 244 emits the electron beam 3a in the X-ray generator 230, the negative bias voltage applied to the selected grid electrode 245 is canceled to obtain the zero potential (or a positive potential), and the electron beam 3a is passed through the hold of each grid electrode 245 and incident upon the target 233. When the electron beam 3a is incident upon the target 233, the target 233 generates the X-ray 3, and emits the X-ray 3 to the subject 5 via the collimator (not shown).

The X-ray generator 230 will next be described in detail with reference to FIGS. 14 to 20.

As shown in FIG. 14, the X-ray generator 230 is contained in the vacuum tube 220 whose whole surface is substantially covered with a shield material 224 formed of a lead plate having a thickness t4 of 3 to 5 mm. The shield material 224 covers a large part of an outer surface of the vacuum tube 220 excluding a portion of a window 220a as an X-ray emission port, so that the X-ray 3 does not leak in a direction other than the space for diagnosis 211a.

Figure 18:
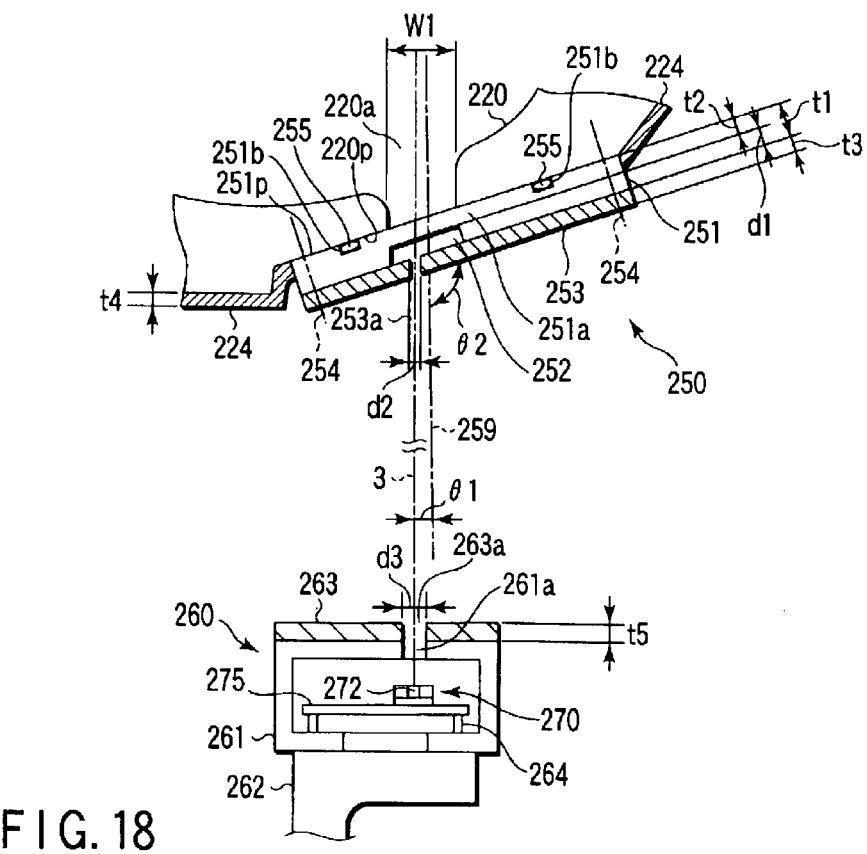
FIG. 18 is an enlarged sectional view showing an X-ray emission portion and detection portion.

As shown in FIG. 18, an X-ray emission portion 250 is attached to the window 220a of the vacuum container. A shield material 253 formed of the lead plate and collimator (not shown) are also attached to the X-ray emission portion 250. In the present embodiment, the plate thickness of the shield material 253 of the X-ray emission portion 250 was set to 5 mm.

As shown in FIGS. 15 and 16, the X-ray generator 230 drives the electron beam 3a into the tungsten target 233 in an anode housing 231 from an electron gun 240 under a vacuum atmosphere, and generates the X-ray 3 from the target 233. An opening portion of the vacuum tube 220 is tightly sealed in order to prevent vacuum inside the tube from being broken. For example, the window 220a is covered with a window member 251 of the X-ray emission portion 250, an abutment surface 251p of the window member and abutment surface 220p of the tube are both mirror-finished, and an O ring 255 is fitted in a seal groove 251b. This secures the air tightness of the vacuum tube 220, and the inside of the vacuum tube 220 can be evacuated to a predetermined vacuum degree (e.g., $1\times10^{-7}$ to $1\times10^{-9}$ Torr).

Figure 19:
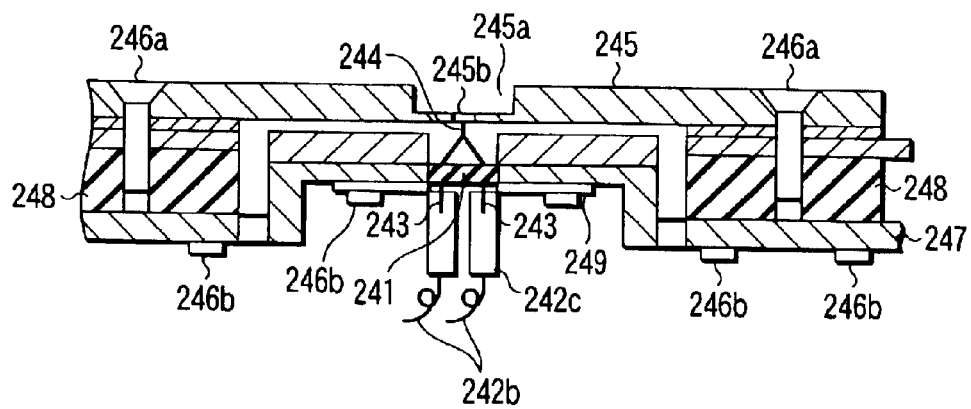
FIG. 19 is an enlarged sectional view showing an electron beam emission portion.

As shown in FIG. 19, the electron gun 240 is supported by an insulating support plate 241 in an insulated state from the peripheral member in the vacuum tube 220. The electron gun 240 includes the cathode 244 and grid electrode 245 formed of a $CeB_6$ or $LaB_6$ monocrystal. The negative bias voltage (e.g., −700 V) is constantly applied to the grid electrode 245. However, with a zero or positive potential, the electron beam 3a is emitted toward the anode target 233 from the cathode electrode 244 through a beam passing hole 245b of the grid electrode 245.

To facilitate the emission of the electron beam 3a, a concentric countersink 245a is formed in the periphery of the beam passing hole 245b. Additionally, in the present embodiment, the thickness of the grid electrode 245 was set to 3 mm. It is preferable to set the thickness of the portion of the countersink 245a to ¼ to ½ of the thickness of the grid electrode 245, the diameter of the beam passing hole 245b is preferably 4 mm, and the diameter of the countersink 245a is preferably 6 mm.

For the grid electrode 245, after laminating an electrically conductive thin film formed of the high-melting metal or alloy such as tungsten, molybdenum, and tantalum on the ceramic ring substrate such as silicon nitride ($Si_3N_4$), silicon oxide ($SiO_2$), silicon carbide (SiC), alumina ($Al_2O_3$), and sialon (SiAlON), the electrically conductive thin film is etched in a predetermined pattern to form the insulating portion. Additionally, after the pattern etching, the electron beam passing hole 245b of the grid electrode is formed by mechanical processing such as drill perforation. Alternatively, to simplify the processing, the stainless steel plate may also be used in the grid electrode.

As shown in FIG. 15, a pair of positive and negative filament current introducing terminals insulated from the periphery by insulators 242a, 242c are connected to the cathode 244 via cables 242b, and a discharge voltage of plus 150 kV is applied to the cathode 244.

As shown in FIG. 19, the cathode 244 is completely insulated from the vacuum tube 220 by the ceramic holder 241. The ceramic holder 241 is fitted in a concave portion of a support frame 247, and a peripheral edge of the holder is pressed onto the support frame 247 by a press plate 249. Moreover, the grid electrode 245 is completely insulated from the vacuum tube 220 by a ceramic ring 248. The ceramic ring 248 is inserted between the grid electrode 245 and support frame 247, a plurality of screws 246a are used to fasten the grid electrode 245 and ceramic ring 248, and a plurality of screws 246b are used to fasten the support frame 247 and ceramic ring 248.

Additionally, it is preferable to use ceramic such as high-purity silicon nitride and high-purity alumina superior in the pressure resistance property in the ceramic holder 241 and ceramic ring 248.

The cathode 244 is of a so-called Cambridge type, and is formed of a monocrystal of a nonmetal compound of $SeB_6$ or $LaB_6$ with a diameter of 1 to 3 mm. The cathode 244 functions as a heater for discharging a thermal electron. That is, when power is supplied to the cathode 244, a high-voltage electric field is concentrated on the tip end of the cathode to generate heat at a high temperature, and the thermal electron is discharged.

The high-voltage electric field is concentrated on the tip end of the cathode 244 and chipping easily occurs. Therefore, a corner edge portion of the cathode is chamfered and rounded. The lower half portion of the cathode 244 is cut from opposite sides, a flat surface is formed, and a pair of positive/negative molybdenum wires 243 are connected to each flat surface so as to press a graphite chip. Base ends of the pair of positive/negative molybdenum wires 243 are connected to positive/negative terminals buried in the insulators 242c, and a high voltage is applied from the external power source 214 via the cables 242b.

The target 233 functions as the anode electrode which generates the X-ray 3, and is disposed in the focal point formed on the surface against which the electron beam 3a emitted from the electron gun 240 collides. The high-speed electron rushes into the target atom and is stopped from moving, and thereby a part of the movement energy is discharged as the X-ray 3. That is, when the electron beam 3a is incident upon the target 233 from the cathode 244, the target 233 emits the X-ray 3 in the fan shape in the direction of reflection in accordance with the angle of the surface. Additionally, the target 233 is formed of a rectangular plate of tungsten or tungsten alloy, and preferably has a thickness in a range of 0.5 to 7.0 mm, width of 8 to 12 mm, and length of 30 to 50 mm. In the present embodiment the thickness of the target 233 was set to 1.0 mm. Moreover, the irradiation surface of the target 233 is inclined by about 20° with respect to an optical axis of the electron beam 3a.

In a theoretical sense, when the electron beam is driven into the target having a thickness of the order of several microns, the X-ray is generated. However, when the thickness of the target is excessively thin, the target easily undergoes fatal damage such as melting, cracking, and chipping. Therefore, it is most preferable to set the thickness of the target to about 1.0 mm. Additionally, if the target is excessively thick, the heating amount increases, and it becomes difficult to cool the target. Therefore, the target is preferably thinned in a tolerable range.

A cooling block 232 is formed of a good conductor superior in thermal conductivity, such as copper and aluminum, holds the target 233 on the inclined surface thereof, and protects the target 233 from any thermal damage. The cooling block 232 is supported by the insulating support member 225 so that the block is insulated from the vacuum container.

An outline of a gate array control circuit will be described.

The anode 233, cathode 244, and grid electrode 245 in the X-ray generator 230 are connected to n pulse generation control ports via n pulse generators disposed in the control apparatus 217. With input of the setting mode signal from the mode setting instructor (not shown), the CPU of the control apparatus 217 sends X-ray generation command signals to the pulse generation control ports in accordance with the set mode, so that the signal is transmitted to the pulse generator corresponding to the pulse generation control port having received the command signal. The negative bias voltage applied to the corresponding grid electrode 245 is canceled to obtain the zero potential. Thereby, the electron beam 3a is passed only through the beam passing hole of the corresponding grid electrode 245, and incident upon the anode 233, and the anode 233 emits the X-ray 3.

The X-ray emission portion 250 will next be described.

As shown in FIG. 18, the X-ray emission portion 250 is attached over the whole circumference of 360° outside the window 220a of the annular vacuum tube 220. The window member 251 of the X-ray emission portion 250 is formed of a material through which the X-ray is easily passed and in which the X-ray has a small attenuation ratio, such as aluminum, beryllium, alloy of aluminum or beryllium, and stainless steel.

A cutout groove 252 is formed in an X-ray passing portion of the window member 251, and forms a thin portion 251a. The cutout groove 252 is formed by using a milling machine over the whole circumference of 360° to cut/process substantially the half of the thickness of the window member 251. A thickness t2 of the thin portion 251a variously changes in accordance with the material of the window member 251, but it is necessary to secure at least a pressure resistant strength with which a negative pressure of the vacuum tube 220 can be withstood. For example, when the window member 251 is formed of an aluminum plate with a plate thickness t1 (=3 mm), the thickness t2 of the thin portion 251a needs to be set to at least 1 mm.

Furthermore, a large part of the window member 251 is covered with the shield material 253 formed of the lead plate. In the shield material 253, beam passages 253a which permit the passage of the X-ray 3 are formed. In the present embodiment, a thickness t3 of the shield material 253 was set to 5 mm, and a diameter d2 of the beam passage 253a was set to 0.5 mm to 3.0 mm. The X-ray 3 is passed only through the beam passage 253a of the shield material 253, narrowed by the collimator (not shown), and emitted. The emitted X-ray 3 is passed through the subject 5, and subsequently detected by the detector 260.

As shown in FIG. 18, in the present embodiment, a diameter W1 of the window 220a of the vacuum tube was set to 20 to 30 mm, and the width of the thin portion 251a of the window member was set to be substantially equal to the diameter W1 of the window 220a. Moreover, a beam tilt angle θ1 formed by the optical axis of the X-ray 3 with a Z-axis 259 (vertical axis) was set to 0.1° to 2.5°. Furthermore, an attachment angle θ2 formed by the window member 251 with the Z-axis 259 (vertical axis) was set to 95° to 105°.

Additionally, in the shield material 253 of the X-ray emission portion, the sectional shape of the X-ray emission hole 253a may be circular, oval or elliptical, or may have a slit shape. With the emission hole having the slit shape, a spacer is preferably disposed in a selected place through which the X-ray beam does not pass in order to hold a constant slit interval.

The detector 260 will next be described.

As shown in FIGS. 18 and 14, the detector 260 is supported by the inner peripheral surface of the vacuum tube 220 via a ring frame 262. The same number (e.g., 4086) of detectors 260 as the number of X-ray generators 230 are disposed so as to have one-to-one correspondence with the X-ray generators 230. These detectors 260 and X-ray generator 230 are slightly shifted in the X-axis direction and arranged, and as shown in FIG. 14 the X-ray 3 is emitted in a slightly forward tilting direction with respect to the radius (Z-axis) of the gantry 211. Therefore, the X-ray 3 is passed through the subject 5 and detected by the detector 260 on the opposite side (below) without being interrupted by the detector 260 on the X-ray emission side (above).

A housing 261 of the detector 260 includes an incidence port 261a, and contains a sensor assembly (detection portion) 270 which is fixed onto the inner peripheral surface of the ring frame 262 by bolts and which includes the CdTe photoelectric conversion device 272 inside. A shield material 263 is attached to the inner peripheral surface of the housing 261. An incidence port 263a is formed in the shield material 263, and the X-ray 3 is passed through the incidence port 263a and the opening 261a of the housing and detected by the CdTe photoelectric conversion device 272.

Additionally, the incidence ports 261a, 263a may have circular, oval, elliptical, or slit shapes. When the incidence ports 261a, 263a have the slit shapes extending over the whole circumference of 360°, a plurality of spacers (not shown) may be disposed in appropriate places in order to keep the constant slit interval.

The sensor assembly (detection portion) 270 includes the CdTe photoelectric conversion device 272 and a printed circuit board 275. The CdTe photoelectric conversion device 272 is formed of a monocrystal of cadmium telluride whose transverse section forms a square columnar rectangular parallelepiped.

4078 CdTe photoelectric conversion devices 272 constituting the sensor array are arranged at equal pitch intervals on the printed circuit board 275 so that light receiving surfaces are aligned at the same height level. The printed circuit board 275 is supported by the ring frame 262 via an insulating support member 264 as shown in FIG. 18, connected to the other end surface (surface opposite to the light receiving surface) of the CdTe photoelectric conversion device 272 via a gold wire bonding (not shown), and further sealed with a resin.

Additionally, the incidence ports 261a, 263a may have various shapes such as circular, oval, elliptical and slit shapes. With the incidence ports 261a, 263a having the slit shapes, the spacers are disposed in the selected places through which the X-ray beams do not pass in order to hold the constant slit intervals.

Additionally, in the present embodiment, the sensor array, anode array, and cathode array are arranged over the whole circumference having a center angle of 360°, but there may be arranged over the half circumference having a center angle of 180°. This is because the image can sufficiently be constituted again based on the transmission X-ray information for the half circumference.

Moreover, in order to avoid undetected transmitted X-rays, the center angle of the arrangement of the sensor array is set to be larger than the center angle of the arrangement of the anode array (or the cathode array) by the spread angle 2α of the fan-shaped X-ray. Additionally, the spread angle 2α of the X-ray is assumed to be in a range obtained from the following inequality. In this case, the center angle of the arrangement of the sensor array is preferably set to be larger by the spread angle 2α of the X-ray, in which tanα indicates a center value of at least 0.375 (=⅜).

$$0.370 \leq \tan\alpha \leq 0.380$$

In the apparatus of the present embodiment using a cathode power source of this 150 kV class, the lead plate with a plate thickness of 5 mm was used in the shield material 263 of the X-ray detector. This can effectively prevent a secondary X-ray or scattered ray from immerging, and a clear diagnosis image can be obtained.

The electron gun 240 will next be described.

As shown in FIG. 19, the electron gun 240 includes the cathode 244 and grid electrode 245 which are insulated from the peripheral members. The cathode 244 is supported by the frame 247 in the insulated state from the periphery by the ceramic holder 241. On the other hand, the grid electrode 245 is supported by the frame 247 in the insulated state from the periphery by the ceramic ring 248. Additionally, in the drawing, reference numerals 246a, 246b denote bolts, and 249 denotes a press plate. The press plate 249 presses the peripheral edge of the ceramic holder 241 onto the concave portion of the frame 247 so that the assembly including the cathode 244 does not fall off the frame 247.

The cathode 244 is of the so-called Cambridge type, and is formed of the monocrystal of the nonmetal compound of $SeB_6$ or $LaB_6$ with a diameter of 1 to 3 mm. The lower half portion of the cathode 244 is cut from the opposite sides, the flat surfaces are formed, and a pair of positive/negative molybdenum wires 243 are connected to the respective flat surfaces so as to press the graphite chip. The base ends of the pair of positive/negative molybdenum wires 243 are connected to the positive/negative terminals buried in the insulators 242c, and a discharge voltage, for example, of plus 150 kV is applied from the power source (not shown) via the cables 242b.

The grid electrode 245 is connected to a direct-current power source via a cable (not shown). The power source supplies a gate voltage of minus 700 V to the grid electrode 245. When the electron beam 3a is emitted toward the anode 233 from the cathode 244, the bias applied to the grid electrode 245 is released, and the grid electrode 245 is set to a zero or positive potential. Thereby, the electron beam 3a is emitted toward the cathode 244, passed through the hole 245b of the grid electrode, and incident upon the anode 233, so that the anode 233 discharges the X-ray 3.

Figure 20:
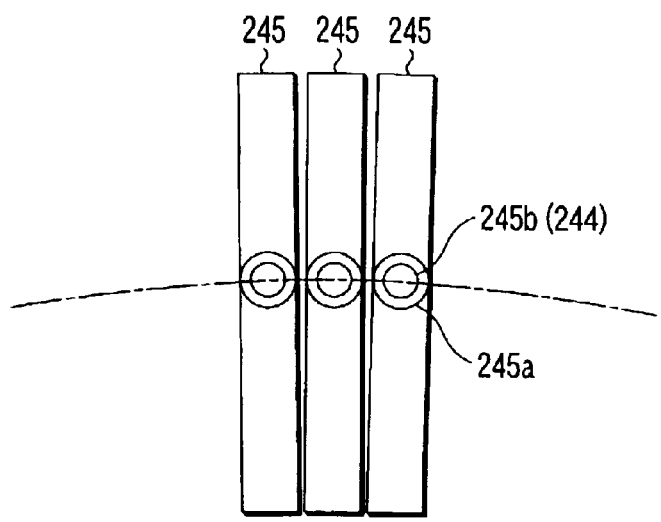
FIG. 20 is a plan view showing a cathode and grid.

As shown in FIG. 20, the grid electrodes 245 are arranged at equal pitch intervals on the circumference which centers on the axial center of the CT apparatus and has a radius of 800 mm. For example, when the number of X-ray generators 230 (targets 233) is 360, the pitch interval of the grid electrode 245 is set to 14 mm, the width thereof is 12 mm, and the length thereof is 100 mm. Moreover, when the number of X-ray generators 230 (targets 233) is 240, the pitch interval of the grid electrode 245 is set to 20.9 mm, the width is 19 mm, and the length is 100 mm.

The beam passing hole 245b is opened/formed in a middle of a longitudinal direction of the grid electrode 245. Additionally, the diameter of the countersink 245a is preferably set to be equal to the width of the grid electrode 245, and the diameter of the beam passing hole 245b is in a range of ⅓ to ½ (30 to 50%) of the diameter of the countersink 245a.

An outline of the operation of the above-described apparatus will next be described.

When the main switch of the apparatus 200 is turned ON, the bias voltage of minus 150 kV (this can also be −20 V) is applied as a voltage sufficient for heating the cathode electrodes 244 at a temperature sufficient for discharging a significant electron amount to the cathode electrodes 244. The bias voltage, for example, of minus 1 kV (this can also be −0.5 kV) is applied to the grid electrodes 245, and the bias voltage of plus 150 kV is applied to the anode electrodes 233. At a predetermined time, the data storage apparatus 218 outputs the command signal indicating the first X-ray generation to the control apparatus 217.

Based on this first command, the command of the first X-ray generation is inputted into the pulse generation control ports in the X-ray generation control apparatus 217. Upon receiving the input signal, two pulse generators simultaneously generate the pulse waves, and supply these pulse signals to the grid electrodes 245 corresponding to the pulse generators. When the pulse generation signals are received, the negative bias voltages of the grid electrodes 245 are canceled to obtain the zero or positive potential, and the electron beams 3a are passed through the holes 245b of the grid electrodes and incident upon the anode electrodes 233.

At a predetermined time, the command of the first X-ray generation ends, the negative bias voltages of the grid electrodes 245 are restored, and the electron beams 3a are again shut off by the grid electrodes 245. For the time, the anodes 233 emit the X-rays 3. In this manner, the operation of successively changing the emission place of the X-ray is repeated.

Additionally, the gate change time is controlled in a range of 2.1 to 20.8 microseconds ($\frac{1}{480,000}$ to $\frac{1}{48,000}$ second). Moreover, the X-ray generation time is controlled in a range of 1.4 to 13.9 microseconds ($\frac{1}{720,000}$ to $\frac{1}{72,000}$ second) which corresponds to $\frac{2}{3}$ of the gate change time.

The generated X-ray 3 is emitted toward the subject 5 disposed in the space for diagnosis 211a. The emitted X-ray 3 is absorbed in accordance with the transmittance of the subject 5, and detected by the detectors 260 disposed opposite to each other.

The X-ray transmission information detected by the detectors 260 is converted to the current or voltage signal proportional to the transmitted X-ray amount, thereafter amplified by the preamplifier 215 and main amplifier 216, and sent as the voltage signal to the data storage apparatus 218.

When the detection operation by the detectors 260 ends, next the command of the second X-ray generation is input into the pulse generation control ports in the control apparatus 217, and the detection operation is performed similarly as described above. Moreover, when the X-ray transmission information obtained from all successively performed detection operations is detected by the detectors 260, the information is converted to the current or voltage signal proportional to the transmitted X-ray amount, and the signal is processed in the data processing apparatus 219 via the preamplifier 215, main amplifier 216, and data storage apparatus 218. The X-ray CT image information of the subject 5 is obtained from the data subjected to the signal processing.

According to the apparatus of the present embodiment, since the array including the ring-shaped cathode/grid/anode insulated from one another is disposed in the annular vacuum tube, the X-ray generation points can more densely be arranged than before, and the X-rays can be emitted in the desired irradiation direction in the vacuum tube. Therefore, the adjacent image pickup intervals are set to be finer. With the increase of the scan speed, the image quality by the space resolution improvement can be enhanced, and it is possible to diagnose the details of the inner structure of the subject.

Third Embodiment

Figure 21:
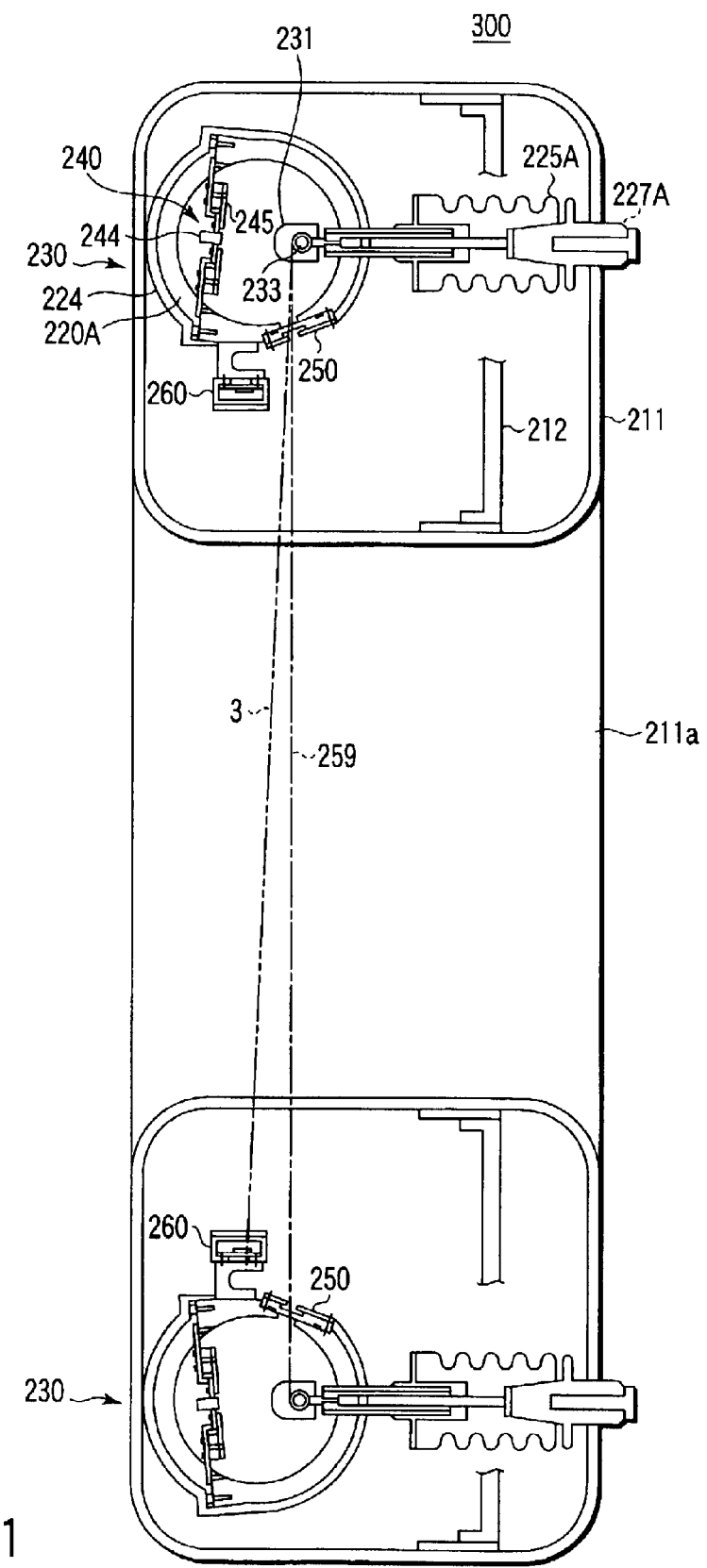
FIG. 21 is an inner perspective sectional view showing the multisource type X-ray CT apparatus (100 kV) according to another embodiment of the present invention.

A multisource type X-ray CT apparatus for 100 kV will next be described as a third embodiment with reference to FIG. 21.

In a multisource type X-ray CT apparatus 300 of the present embodiment, to supply power to the anode target 233, a source-side terminal 227A is screwed/connected into the terminal of the electrode rod 228 insulated by an insulator 225A. The tip end of the electrode rod 228 is pressed onto the power supply point 234a of the anode block (see FIG. 17). Thereby, the power source 214 supplies a direct-current power of 100 kV to the anode target 233 (see FIG. 10).

The insulator 225A is formed of high-purity alumina, and has a pressure resistant capability of 150 kV. The insulator 225A is different from the insulator 225 of the first embodiment in the shape and size with respect to the installation structure, and has advantages that hot air is absorbed and the insulator can easily be mass produced.

The apparatus of the present invention can be applied to any image diagnosis in medical and industrial fields. According to the present invention, a high space resolution can be fulfilled in a limited installation space, and manufacturing and running costs can be reduced. Moreover, with an increase of scan speed, an image quality by space resolution improvement can be enhanced, and it is possible to diagnose details of an inner structure of a subject. Therefore, in the medical field, heartbeats of an arrhythmia time, motion of a coronary artery, detection of abnormal tissues inside the lungs, blood flows, and the like can be reconstituted as clear images. Moreover, in the industrial field, movement of a fluid phase of a two-phase flow including solid-liquid, gas-liquid, or solid-gas, movement of multi-component system fluid phase, phase change, and the like can also be reconstituted as the clear images.

What is claimed is:

1. A multisource type X-ray CT apparatus comprising:
   a sensor array including a plurality of detection devices densely fixed on a circumference which surrounds a subject in order to detect X-rays transmitted through the subject;
   a vacuum chamber fixed so as to surround the sensor array coaxially with arrangement of the sensor array; and
   an X-ray generation unit which is disposed in the vacuum chamber and which emits the X-rays toward the subject surrounded by said sensor array,
   wherein said X-ray generation unit includes:
      a cathode which is disposed in one circuit in said vacuum chamber so as to surround the sensor array coaxially with the arrangement of said sensor array and which has a tip portion that emits electron beams by power supply;
      an anode disposed in a position upon which the electron beams emitted from said cathode are incident, and disposed in said vacuum chamber so as to surround the sensor array coaxially with the arrangement of said sensor array, so that the electron beams are received and the X-rays are emitted;
      a gate array including a plurality of grid electrodes which are densely arranged between said cathode and anode and which is insulated from at least the cathode, the grid electrodes being insulated from one another and arranged at equal pitches in one circle;
      a beam passing hole which is open in a middle of each of the grid electrodes in a longitudinal direction so as to face the tip portion of the cathode and which allows passage of the electrode beams emitted from the cathode;
      a countersink formed around the beam passing hole in each of the grid electrodes;
      a power source which applies a bias voltage to the grid electrodes of said gate array; and
      control means for controlling a power supply operation from said power source so as to select the grid electrode suitable for image pickup from said gate array in accordance with an image pickup portion of the subject and to release the bias voltage applied to the selected grid electrode.

2. An apparatus according to claim 1, wherein said gate array includes 60 to 240 grid electrodes, and an insulating portion to insulate the grid electrodes disposed adjacent to each other.

3. An apparatus according to claim 1, wherein said gate array includes 150 to 300 grid electrodes, and an insulating portion to insulate the grid electrodes disposed adjacent to each other.

4. An apparatus according to claim 1, wherein said gate array includes 240 to 500 grid electrodes, and an insulating portion to insulate the grid electrodes disposed adjacent to each other.

5. An apparatus according to claim 1, wherein the countersink has a diameter equal to a width of the grid electrode.

6. An apparatus according to claim 1, wherein the beam passing hole has a diameter in a range from $\frac{1}{3}$ to $\frac{1}{2}$ that of the countersink.

7. An apparatus according to claim 1, wherein the beam passing hole has a diameter in a range from 30% to 50% that of the countersink.

* * * * *